United States Patent
Kask

(10) Patent No.: US 6,690,463 B2
(45) Date of Patent: Feb. 10, 2004

(54) FLUORESCENCE INTENSITY AND LIFETIME DISTRIBUTION ANALYSIS

(75) Inventor: Peet Kask, Harku (EE)

(73) Assignee: Evotec BioSystems AG, Hamburg (DE)

( * ) Notice: Subject to any disclaimer, the term of this patent is extended or adjusted under 35 U.S.C. 154(b) by 0 days.

(21) Appl. No.: 09/779,704

(22) Filed: Feb. 9, 2001

(65) Prior Publication Data

US 2002/0063863 A1 May 30, 2002

Related U.S. Application Data

(60) Provisional application No. 60/181,548, filed on Feb. 10, 2000.

(51) Int. Cl.[7] .................................................. G01J 3/30
(52) U.S. Cl. .................. 356/317; 250/458.1; 250/459.1; 356/311
(58) Field of Search .................... 356/317, 311, 356/318, 416, 417, 419, 420; 250/458.1, 459.1, 461.1, 461.2; 422/82.05, 82.07, 82.08; 436/172; 435/288.7

(56) References Cited

U.S. PATENT DOCUMENTS

| | | | |
|---|---|---|---|
| 6,137,584 A | * 10/2000 | Seidel et al. | 356/445 |
| 6,376,843 B1 | * 4/2002 | Palo | 250/458.1 |
| 6,515,289 B1 | * 2/2003 | Kask | 250/459.1 |
| 6,556,296 B1 | * 4/2003 | Palo | 356/317 |

FOREIGN PATENT DOCUMENTS

| | | | |
|---|---|---|---|
| EP | 0 836 090 A1 | 4/1998 | |
| EP | 884583 A1 | * 12/1998 | G01N/21/64 |
| WO | WO 93/19358 | 9/1993 | |
| WO | WO 99/17086 | 4/1999 | |

* cited by examiner

*Primary Examiner*—Thong Nguyen
*Assistant Examiner*—Arnel C. Lavarias
(74) *Attorney, Agent, or Firm*—Jacobson Holman PLLC

(57) ABSTRACT

The present invention relates to a method for characterizing samples having fluorescent particles, comprising the steps of:

exciting particles in a measurement volume to emit fluorescence by a series of excitation pulses, monitoring the emitted fluorescence by detecting sequences of photon counts using a detector, determining numbers of photon counts in counting time intervals of given width, determining in the counting time intervals detection delay times of the photon counts relative to the corresponding excitation pulses, determining a function of the detection delay times, determining a probability function of at least two arguments, $\hat{P}(n, t, \ldots)$, wherein at least one argument is the number of photon counts and another argument is the function of detection delay times, and determining from the probability function $\hat{P}(n, t, \ldots)$ a distribution of particles as a function of at least two arguments, wherein one argument is a specific brightness of the particles, or a measure thereof, and another argument is a fluorescence lifetime of the particles, or a measure thereof.

24 Claims, 8 Drawing Sheets

FLUORESCENCE INTENSITY AND LIFETIME DISTRIBUTION ANALYSIS

This application claims priority from and the benefit of U.S. Provisional application Serial No. 60/181,548, filed on Feb. 10, 2000.

The present invention relates to a method for characterizing samples having fluorescent particles and applications of said method.

The utilization of fluorescence has evolved rapidly during the past decades because it offers high sensitivity in various scientific applications. New developments in instrumentation, data analysis, probes and employment have resulted in enhanced popularity for a technique that relies on a phenomenon discovered nearly 150 years ago (Stokes, Phil. Trans. R. Soc. Lond. 142, 463–562, 1852). In a number of applications in physical chemistry, biology and medicine, fluorescence is used as a sensitive means of detecting chemical binding reactions in dilute solutions. Drug screening and pharmaceutical assay development are examples of fields of applications of this kind.

In addition to classical methods based on detecting changes in macroscopic fluorescence characteristics such as overall intensity or anisotropy, a number of different fluctuation methods have been developed during the last decades distinguishing species on ground of properties characteristic to single molecules. One of the most elaborated fluorescence techniques with single molecule sensitivity is fluorescence correlation spectroscopy (FCS) that can resolve different species first of all on the basis of different translational diffusion coefficient (Magde et al., Phys. Rev. Lett. 29, 104–708, 1972; Elson et al., Biopolymers 13, 1–27, 1974; Rigler et al., Eur. Biophys. J 22, 169–175, 1993). Recently, this fluorescence fluctuation method found its counterpart in fluorescence intensity distribution analysis (FIDA) that discriminates different fluorescent species according to their specific brightness (Kask et al., Proc. Natl. Acad. Sci. USA 96, 13756–13761, 1999). The term "specific brightness" generally denotes the mean count rate of the detector from light emitted by a particle of given species situated in a certain point in the sample, conventionally in the point where the value of the brightness profile function is unity.

Aside methods like FCS and FIDA which distinguish species on the ground of a single specific physical property, two-dimensional methods have been developed, utilizing two detectors monitoring different polarization components or emission bands of fluorescence. In particular, fluorescence cross-correlation analysis and two-dimensional fluorescence intensity distribution analysis (2D-FIDA) are methods recognizing species on the ground of two types of specific brightness (Kask et al., Biophys. J. 55, 213–220, 1989; Schwille et al., Biophys J. 72, 1878–1886, 1997; Kask et al. Biophys. J. 78, 2000).

While FCS, FIDA and the mentioned two-dimensional methods are statistical methods of fluctuation spectroscopy, there is also another broad field of research having the goal to identify individual molecules. Many applications make use of the fluorescence lifetime as an intrinsic molecular property that is sensitive to any changes of the molecule's direct environment. However, different from the above mentioned fluctuation methods, fluorescence lifetime analysis (FLA) is basically a macroscopic technique that allows the discrimination of different fluorescence decay times without the need for molecular number fluctuations in the monitored sample volume. Therefore, fluorescence lifetime measurements are usually performed in cuvettes at high sample concentrations. However, the disadvantage of this implementation is that the experimentally collected excitation to detection delay time histogram has contributions from different species which are difficult to be resolved. In addition, FLA has only a low robustness—slightly wrong assumptions yield very wrong results.

On the contrary, lifetime experiments have also been applied to extremely low mean particle numbers. This approach, being opposed to conventional FLA, was introduced as burst integrated fluorescence lifetime analysis (BIFL) (Keller et al., Applied Spectroscopy 50, 12A–32A, 1996). BIFL searches for fluorescence bursts from single molecules above a certain threshold intensity. Its disadvantage is that it can only be applied at very low concentrations of significantly less than one particle per measurement volume and therefore relatively long data collection time is needed.

In fluorescence lifetime experiments, if performed in the time domain with time correlated single photon counting (TCSFC), the excitation to detection delay time, t, of single photons is recorded and collected in a histogram. To extract the fluorescence lifetime a theoretical distribution P(t) is fitted against these experimental data. Usually P(t) is described by a single- or multi-exponential decay function that is convoluted with the respective instrument response function (IRF). Whereas this kind of analysis allows to characterize constituents of the sample according to their individual lifetimes, $\tau$, it does not allow the determination of their concentrations, c, and specific brightness, q, but only the products, qc.

Therefore, it is an object of the present invention to provide a method of high accuracy and robustness which allows the characterization of individual particles based on their fluorescence properties.

According to the present invention, a method for characterizing samples having fluorescent particles is presented which comprises the following steps. At first particles in a measurement volume are excited by a series of excitation pulses and the emitted fluorescence is monitored by detecting sequences of photon counts. For this purpose, a confocal epi-illuminated microscope might preferably be used in connection with a high repetition rate (e.g. 100 MHz) laser pulse excitation. Numbers of photon counts in counting time intervals of given width are determined as well as the detection delay times of the photon counts relative to the corresponding excitation pulses. A function of said detection delay times is built—as described in detail below—and as a next step a probablity function of at least two arguments, $\hat{P}(n, t, \ldots)$ is determined, wherein at least one argument is the number of photon counts and another argument is said function of detection delay times. Thereafter, a distribution of particles as a function of at least two arguments is determined on basis of said probability function $\hat{P}(n, t, \ldots)$, wherein one argument is a specific brightness (or a measure thereof) of the particles and another argument is a fluorescence lifetime (or a measure thereof) of the particles. The method according to the present invention, called Fluorescence Intensity and Lifetime Distribution Analysis (FILDA) has the advantage that it is possible to determine absolute concentrations, a quantity that is not directly accessible with conventional FLA. The combined information, when used in such a correlated manner according to the present invention, results in significantly increased accuracy as compared to FIDA and fluorescence lifetime analysis alone. In contrast to BIFL, that searches for fluorescence bursts from single molecules above a certain threshold intensity, FILDA analyses preferably the relative fluctuations of the whole data stream and thus accounts for the possibility of simultaneous photon emission from different molecules. Therefore, the present invention can also be used at significantly higher concentrations than BIFL.

In the following, the underlying theory as well as preferred embodiments are elaborated and applied to simulated as well as experimental data. The outstanding power in resolving different species is shown by quantifying the binding of calmodulin to a peptid ligand, promising a broad applicability in the life sciences.

As outlined above, the present invention relies on a method which is at least two-dimensional: different fluorescent particle species in the sample are distinguished from each other by specific brightness as well as lifetime values. In some cases it might however be advantageous to take into consideration further particle properties, such as their diffusion coefficient or brightness in respect to two different photon detectors monitoring fluorescence of different colour or polarization. In these cases, the method of the present invention is of a higher dimension than merely two-dimensional, which is denoted by the dots in the formula of the probability function. However, for the sake of simplicity most of the following explanations will be elaborated on a two-dimensional case.

According to the present invention, a method has been developed that is suited to discriminate different species of a sample according to their lifetimes, $\tau$, and brightness values, q, as well as to determine their absolute concentrations, c. The key is to analyze a measured two-dimensional FILDA distribution $\hat{P}(n,t)$ of the number of detected photon counts n and the integrated delay time t, applying a theoretical expression of the expected distribution $P(n,t)$. In the following, an extension of the theory of FIDA (Kask et al., Proc. Natl. Acad. Sci. USA 96, 13756–13761, 1999) will be presented that results in a fast and efficient algorithm capable to fit the measured two-dimensional FILDA distribution. Using the representation of the generating functions, the problem is at first reduced to that of single species. In the case of single species, $P(n,t)$ is expressed as a product of two factors, $P(n)$, which is the photon count number distribution, and $P(t|n)$, which is the integrated delay time distribution over n photon counts. Since the calculation of $P(n)$ is solved by the theory of FIDA and that of $P(t|n=1)=P(t)$ by the theory of FLA, one additionally only needs to calculate $P(t|n)$ from $P(t|1)$.

A major preferred constituent part of the FILDA theory according to the present invention is the concept of generating functions. The generating function of the probability distribution $P(n,t)$ is defined as $$G(\xi, \eta) = \sum_{n=0}^{\infty} \sum_{i=0}^{\infty} P(n, t) \xi^{ji} \eta^j. \tag{1}$$

The detection delay time, t, of each photon is represented in discrete intervals. In this definition, it is convenient to select arguments of the generating function, $\xi$ and $\eta$, in the form $e^{i\Phi}$. Because of this selection $G(\xi,\eta)$ and $P(n,t)$ are interrelated by a two-dimensional Fourier transform which can be calculated by fast algorithms (Brigham, The Fast Fourier Transform, Prentice-Hall, Englewood Cliffs, N.J., 1974).

The reason why the representation of the generating function is convenient becomes clear when comparing how different contributions are included in $P(n,t)$ and $G(\xi,\eta)$. For example, if one has two independent fluorescent species which would separately yield distributions $P_1(n,t)$ and $P_2(n,$ t), then the resulting distribution is expressed as a convolution $$P(n, t) = \sum_{u=0}^{n} \sum_{v=0}^{j} P_1(u, v) P_2(n-u, t-v), \tag{2}$$

while in the representation of the generating function, the relation is expressed as a simple product $$G(\xi,\eta)=G_1(\xi,\eta)G_2(\xi,\eta). \tag{3}$$

The calculation of convolutions is very time-consuming but the calculation of a product is fast and easy. Furthermore, the generalization of Eq. 3 to more than two species is straightforward. The knowledge of a theoretical description of a single species is already sufficient, because Eq. 3 simply expands this description by a product to the case of several components. Therefore, in the following the case of a single species will be considered.

The probability distribution of the detection delay time of each photon may be considered as a function which is characteristic for the given species, depending neither on the number of photons emitted or detected previously nor on the coordinates of the molecule emitting the photon. This means that $P(n,t)$ can be presented as $$P(n,t)=P(n)P(t|n), \tag{4}$$

where $P(t|n)$ is the probability distribution of the integrated detection delay time of n photons and $P(n)$ is the probability distribution to detect n photons within the given counting time interval. Since $P(t|n)$ is calculated from $P(t|1)$ by the n-fold convolution, it can be deduced from Eq. 3 that the one-dimensional generating function of $P(t|n)$ is the n-th power of the generating function of $P(t|1)$:

$$G(\eta|n)=[G(\eta|1)]^n. \tag{5}$$

Substitution of Eqs. 4 and 5 into Eq. 1 leads to the following expression, $$G(\xi, \eta) = \sum_n P(n)[G(\eta|1)]^n \xi^n \tag{6}$$

$$= G(\xi G(\eta|1)). \tag{7}$$

According to Eq. 6, each column of the $G(\xi,\eta)$-matrix, corresponding to a given $\eta$ value, is a one-dimensional Fourier transform of the function $P(n)[G(\eta|1)]^n$, while according to Eq. 7, each element of the $G(\xi,\eta)$-matrix can also be expressed as a Fourier image of $P(n)$ at the point $\xi G(\eta|1)$.

$G(\eta|1)$ is the generating function (here: the one-dimensional Fourier transform) of the expected detection delay time distribution of a photon $P(t|1)$ originating from the particular species. The function $P(t|1)$ is the cyclic convolution of the IRF and an exponential function with a decay time characteristic for the given species.

The issue of how $P(n)$ is calculated has been described by Kask et al. (Proc. Natl. Acad. Sci. USA 96, 13756–13761, 1999; the contents of which are herein incorporated by reference) $P(n)$ is calculated with the help of its generating function which in the case of single species is expressed as $$G(\xi)=exp[c\int(e^{(\xi-1)qTB(r)}--1)dV], \tag{8}$$

where $B(r)$ is the spatial brightness function, q is the apparent specific brightness, T is the width of the counting time interval, c is the apparent concentration, and dV is a volume element. The integral on the right side of Eq. 8 can be calculated numerically. The relationship between the spatial brightness and the corresponding volume elements (needed in the calculation of the right side of Eq. 8) is preferably expressed by an empirical formula of three adjustment parameters $a_1$, $a_2$, and $a_3$, $$\frac{dV}{du} = A_0(1 + a_1 u + a_2 u^2) u^{a_3}, \tag{9}$$

where $u=\ln[B(0)/B(r)]$ and $A_0$ is a coefficient used to select the unit of volume. However, the relationship between the spatial brightness B and volume elements dV might also be expressed by a relationship $$\frac{dV}{du} = A_{0u}(1 + a_1 u + a_2 u^2).$$

The relationship between the true and the apparent concentrations and between the true and apparent specific brightness is presented in the theory of FIMDA (Palo et al., Biophys. J. 79, 2858–2866, 2000: the contents of which are herein incorporated by reference).

In the following, a theory is presented predicting how $c_{app}$ and $q_{app}$ depend on T. The case of single species is studied and the first and the second factorial cumulants of the distribution corresponding to Eq. 3 are calculated. The factorial cumulants are defined as $$K_n = \left(\frac{\partial}{\partial \xi}\right)^n \ln(R(\xi))\bigg|_{\xi=1} \tag{9a}$$

yielding:

$$K_1 = \langle n \rangle = c_{app} q_{app} T, \tag{9b}$$

$$K_2 = \langle n(n-1) \rangle - \langle n \rangle^2 = c_{app} q_{app}^2 T^2, \tag{9c}$$

where normalization coniditions $$\int B dV = 1, \tag{9d}$$

$$\int B^2 dV = 1. \tag{9e}$$

have been used. (Note that Eqs. 9b and 9c are in total agreement with Qian and Elson's formulae (Biophys. J. 57:375–380, 1990).) From Eq. 9b one can conclude that $$c_{app}(T) q_{app}(T) = \langle I \rangle, \tag{9f}$$

where $[I]=[n]_T/T$ is the mean count rate, which does not depend on the choice of T. One shall proceed by employing the following relationship between the second cumulant of the count number distribution $P(n;T)$ and the autocorrelation function of fluorescence intensity $G(t)=\langle I(0)I(t)\rangle - \langle I \rangle^2$, $$\langle n(n-1) \rangle_T - \langle n \rangle_T^2 = \int_0^T dt_1 \int_u^T dt_2 G(t_2 - t_1). \tag{9g}$$

Introducing the notation $$\Gamma(T) = \frac{1}{c_{app}(0) q_{app}^2(0) T^2} \int_0^T dt_1 \int_0^T dt_2 G(t_2 - t_1), \tag{9h}$$

one gets from Eqs. 9g and 9c $$c_{app}(T) q_{app}^2(T) = c_{app}(0) q_{app}^2(0) \Gamma(T). \tag{9i}$$

From Eqs. 9f and 9i one gets $$c_{app}(T) = \frac{c_{app}(0)}{\Gamma(T)}. \tag{9j}$$

$$q_{app}(T) = q_{app}(0) \Gamma(T), \tag{9k}$$

As the final step of deriving the theoretical expression of the generating function of P(n,t) for single species, Eq. 7 and 8 are combined yielding:

$$G(\xi, \eta) = \exp[c \int dV (\exp\{[\xi G(\eta|1)-1] q B(r)T\}-1)] \tag{10}$$

Eq. 10 is a compact theoretical expression. The dependence of $G(\xi,\eta)$ on the fluorescence lifetime is expressed solely by the function $G(\eta|1)$. However, it may be even more transparent from Eq. 6 than from Eq. 10 that two one-dimensional distributions P(n) and P(t|1) fully determine the result $G(\xi, \eta)$ for single species. For multiple species, Eqs. 3 and 10 yield $$G(\xi, \eta) = \exp\left[\sum_i c_i \int dV (\exp\{[\xi G_i(\eta|1) - 1] q_i B(r)T\} - 1)\right] \tag{11}$$

where the subscript i denotes different species.

Discrete Fourier transform algorithms can be used when calculating generating functions from probability distributions or vice versa. This means the distribution function is artificially considered as a function of cyclic arguments. Therefore, cycle periods should be defined. In the count number dimension, it is convenient to define the period at a value of n where P(n) has dropped to practical zero. In the detection delay time dimension, two different period values should be considered.

When P(t|1) is calculated, the selected period of the cycle should coincide with the period of the laser excitation. Here it is taken into account that the fluorescence decay function need not to be dropped to zero during a pulse period, $N_1$. After P(t|1) is calculated in the period of successive excitation pulses $0<t\leq N_1$, the function is padded by zeros in the interval $N_1 \leq t < N_1$, where $N_1$ denotes the value of the cycle period of P(n,t) in t-dimension. A value of $N_1$ is selected where the distribution P(n,t) has dropped to practical zero. Thereafter, Eq. 6 is applied to calculate the Fourier image of P(n,t).

As was explained above, when P(t|1) and its generating function are calculated, the selected period of the probability distribution should naturally coincide with the period of laser excitation. Assuming that the pulse period is divided into $N_1$ detection delay time intervals of width $\Delta$, the ideal periodized probability distribution corresponding to a δ-excitation is expressed in the interval $0<t\leq N_1$ as $$P_\delta(t) = \frac{1 - e^{-\Delta/t}}{1 - e^{-N_i \Delta/t}} e^{-i\Delta/t} \tag{11a}$$

τ denotes lifetime of fluorescence. The easiest way to calculate the convolution of $P_S(t)$ with the time response function R(t) (which is a periodized function as well) is through the Fourier transform:

$$G_{P(t|1)}(\eta) = G_{P_S(t)}(\eta) G_{R(t)}(\eta). \tag{11b}$$

For the sake of precision, P(t|1) can be calculated with a high time resolution. One might e.g. use 8 times higher resolution here, as it was done in experiment 2 described below. After P(t|1) is calculated in the interval $0<t\leq N_1$, the function is amended by a series of zeros in the interval $N_1 \leq t < N_1$. Here $N_1$ denotes the value of periodization of P(n,t) in t-dimension.

Weights of Fitting

For simplification one may assume that count numbers in consecutive counting time intervals are independent. This assumption is not strictly correct because molecular coordinates are significantly correlated over a few counting intervals, but it can nevertheless be successfully applied. Under this assumption, the number of events with a given pair (n,t) is binomially distributed around the mean, M P(n,t), where M is the number of counting time intervals per experiment. This yields the following expression for weights, W(n,t), of the least squares problem $$\chi^2 = \sum_{n,t} W(n,t) \left[\hat{P}(n,t) - P(n,t)\right]^2 = \min$$

$$W(n,t) = \frac{M}{P(n,t)} \quad (12)$$

where $\chi^2$ is the least square parameter, $\hat{P}(n,t)$ is the measured FILDA histogram, and P(n,t) is the theoretical distribution.

The weights, W(n,t), of Eq. 12 are sufficiently good for fitting but would result in underestimated statistical errors if used for this purpose. Therefore, statistical errors of FILDA have been determined from fitting a series of experimental and simulated data.

Coming back to the invention in more general aspects, it shall be mentioned that the second argument of the probability function is not the mere individual detection delay time of each photon, but rather a function thereof such as an integrated detection delay time over all detected photons in a given counting time interval. Note that a molecule can hardly emit two photons from a single excitation pulse, but in the examples presented below, there are 10,000 excitations pulses per a counting time interval, which explains why one can detect tens of photons from a single molecule during that time. This advantageous choice of the second argument is related to the property of fluorescence that a series of photons detected in a short time interval are likely to be emitted by a single molecule, in particular if the optimal concentration for performing the present method is used which is only slightly below one molecule per measurement volume. In classical lifetime analysis this information is lost. For this reason, the method according to the present invention turns out to be a more accurate method of analysis, even if specific brightness values of two particle species present in the sample happen to be identical.

In a preferred embodiment, said function of detection delay times is invariant in respect of the order of detection delay times of photon counts detected in the same counting time interval. Preferably said function of detection times is a sum or a mean. The detection delay times of each photon, i.e. the detection times of photon counts relative to the corresponding excitation pulses, might be expressed by integer numbers having a known relationship to the detection times. This relationship is in ideal a quasi-linear one. The function of detection delay times might preferably be a sum or a mean of said integer numbers.

In a further preferred embodiment, the distribution function of particles is determined by fitting the experimentally determined probability function $\hat{P}(n, t, \ldots)$ by a corresponding theoretical probability function $P(n, t, \ldots)$. This theoretical distribution function $P(n,t, \ldots)$ is preferably calculated through its generating function $$G_{P(n,t,\ldots)}(\xi, \eta, \ldots) = \sum_{n=0}^{\infty} \sum_{t=0}^{\infty} \xi^n \eta^t \ldots P(n, t, \ldots).$$

In the case of a single detector, the experimentally determined probability function is a two-dimensional function, as explained above; thus, it is preferred to determine said distribution function of particles by fitting the experimentally determined probability function $\hat{P}(n,t)$ by a corresponding theoretical probability function P(n,t). The latter is preferably calculated through its generating function $$G_{P(n,t)}(\xi, \eta) = \sum_{n=0}^{\infty} \sum_{i=0}^{\infty} \xi^n \eta^t P(n, t).$$

As far as the present invention is performed by fitting a measured two-dimensional distribution of the number of photon counts (n) and the preferably integrated detection delay time (t), the basic issue is a formula of calculation of the theoretical probability distribution P(n,t). Both arguments of the probability distribution are typical examples of additive variables: for example, if a molecule emits $n_1$ photons with integrated detection delay time $t_1$ and another molecule emits emits $n_2$ photons with integrated detection delay time $t_2$, then they together emit $n_1+n_2$ photons with integrated detection delay time $t_1+t_2$. In this case, it is appropriate to select a representation of the generating function when expressing the probability distribution of interest, as described above.

It is further preferred to determine a temporal response function of the experimental equipment which is to be considered in the calculation of the theoretical distribution P(n, t, . . . ). The temporal response function can be determined from a separate experiment.

In a further preferred embodiment, a set of different values of said width of counting time intervals is used, said width being another argument of said probability function. In this particular case, the diffusion coefficient (or a measure thereof) of the particles can advantageously be determined. Consequently, it becomes a third argument of said distribution function of particles. This embodiment of the present invention is called Fluorescence Intensity Lifetime Multiple Distribution Analysis (FILMDA).

The counting time intervals might be consecutive in time or they might overlap.

As was mentioned above, it is preferred to select concentrations of particles to be approximately one or less molecules per measurement volume. Experiments if performed at significant lower concentrations than one particle per measurement volume would result in a slow acquisition of meaningful information because most of the data collection time is spent on waiting, i.e. with no particles in the measurement volume. This would be a situation which is especially disliked in high throughput screening experiments.

A single, two or more photon detectors are used as said detection means, preferably being either an avalanche photodiode or a photomultiplier. At least two photon detectors can e.g. be used to monitor fluorescence of different colour or polarization.

The method according to the present invention is particularly suited for performing high throughput screening assays, assay development and diagnostic purposes. However, it can be applied widely in life sciences and related technologies.

According to the present invention, confocal techniques are particularly suited to monitor fluctuating intensity of fluorescence. They may be applied—as outlined above—to a wide field of applications, such as biomedicine, etc. The conjugate focal (confocal) technique is based on using a point source of light sharply focused to a diffraction-limited spot on the sample. The emitted light is viewed through a spatial filter (pinhole) that isolates the viewing area to that exactly coincident with the illuminating spot. Thus, the illumination and detection apertures are optically conjugated with each other. Light originating from focal planes other than that of the objective lens is rejected, which effectively provides a very small depth of field. Therefore, in a particular preferred embodiment of the present invention, a confocal microscope is used for monitoring the intensity of fluorescence. In order to achieve a high signal-to-noise-ratio, it is useful to monitor fluorescence using an apparatus that comprises: a radiation source (12) for providing excitation radiation (14), an objective (22) for focussing the excitation radiation (14) into a measurement volume (26), a detector (42) for detecting emission radiation (30) that stems from the measurement volume (26), and an opaque means (44) positioned in the pathway (32) of the emission radiation (30) or excitation radiation (14) for erasing the central part of the emission radiation (30) or excitation radiation (14). It might be particularly preferred to use an optical set-up described in detail in FIG. 6.

Compared to known multi-dimensional fluorescence fluctuation methods, the method according to the present invention is very special since the second stochastic variable of the histogram (or probability function) is preferably the sum or mean of excitation to detection delay times over the number of photons detected in a given counting time interval. If taken alone, this variable has little if any value. It acquires its meaning only when connected with the number of photon counts. A straightforward selection of the two variable when combining brightness and lifetime analysis would be the number of photon counts and each individual excitation to detection delay time; however, the choice of the present invention creates a method of a significantly better accuracy than the straightforward selection. Another reason of the success of this special selection is that the fit function of the histogram (or probability function) can be calculated fast through its Fourier transform, i.e. using the representation of the generating functions.

BRIEF DESCRIPTION OF THE DRAWINGS

The invention is illustrated by the following figures and examples, which are not intended to limit the scope of the invention.

EXPERIMENT 1

Materials and Methods

Experimental Equipment

Figure 1A:
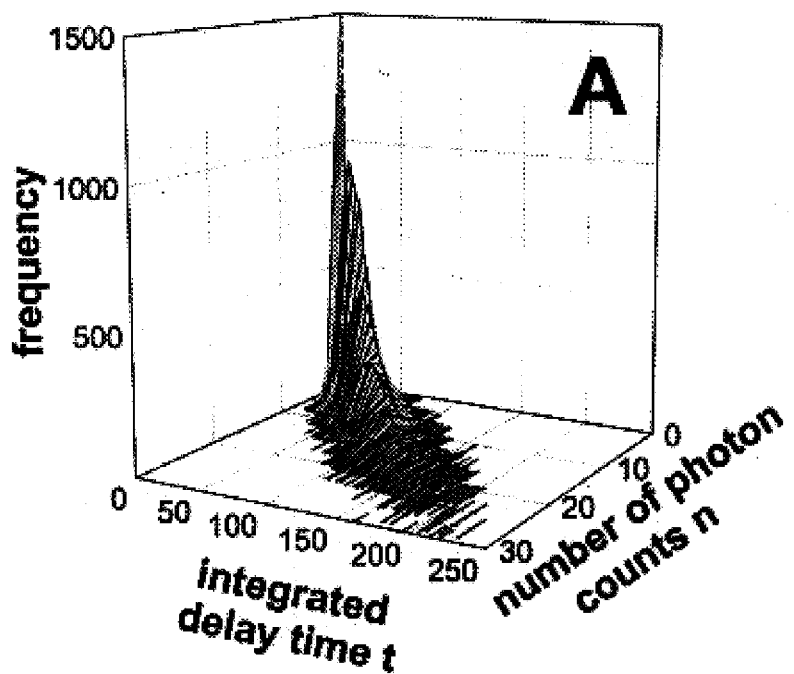
FIG. 1: (A) FILDA histogram from a Bodipy630/650 solution with a data collection time of T=2 s. (B) Weighted residuals of the fit of Eq. 10 to the FILDA histogram of (A) (weighting according to Eq. 12). The fit resulted in values of c=2.3, q=23.2 kHz, τ=3.3 ns, and $\chi^2$=1.1.

A standard epi-illuminated confocal microscope (ConfoCor; EVOTEC BioSystems and Carl Zeiss, Germany) as it is used in fluorescence correlation spectroscopy (Rigler et al., Eur. Biophys. J. 22, 169–175, 1993; Koppel et al., Biophys. J. 16, 1315–1329, 1976) is the central optical part of the present FILDA experiment according to the invention. Since FILDA combines both, continuous specific brightness and time-resolved fluorescence lifetime analysis, a fast pulsed laser diode (Crystal GmbH, Berlin, Germany, 635 nm, 1 mW) is used for excitation. With a repetition rate of 100 MHz it appears as a quasi continuous wave for the intensity fluctuation detection, whereas the according pulse distance of 10 ns at a pulse width of 1.5 ns also allows a sufficiently precise examination of the fluorescence lifetime of the dyes used (Cy5, Oxazine dye MR121, Oxazine dye EVOblue30, Bodipy630/650).

For the excitation of fluorescence the laser light passes a beam expander and is directed to the microscope objective (UApo/340, 40×, N.A. 1.15, Olympus Optical Co. Ltd, Tokyo, Japan) by a dichroic mirror (635LP, Chroma, Brattleboro, Vt., USA). Fluorescence is collected by the same objective through the dichroic mirror, a spectral bandpass filter (670DF40, Omega, Brattleboro, Vt., USA), and is focused to a confocal pinhole, which serves to reject out-of-focus light. The light which passes the 70 $\mu$m pinhole is detected by a silicon photon counting avalanche diode (SPCM-AQ-131, EG&G Optoelectronics, Vaudreuil, Quebec, Canada).

Detector pulses as well as laser trigger pulses are passed to a computer plug-in card. This card constructed at EVOTEC consists of two sub-units one of which is a time correlated single photon counting (TCSPC) module. This module is detecting the delay time of a photon count with respect to the incident laser pulse. A time-to-digital converter (TDC) quantifies this time information with a resolution of 70 ps and a conversion rate of 2 MHz. The other sub-unit is an electronic counter using an internal clock with a time resolution of 50 ns to obtain the time lack between any pair of successively detected photon counts (photon interval time). Thus, two independent times are simultaneously recorded for every detected photon count: the microscopic delay time (ns) of the photon counts with respect to the according laser pulses containing the fluorescence lifetime information and the macroscopic photon interval time ($\mu$s to ms) encoding the fluorescence intensity and fluctuation information. From these fluorescence raw data two one-dimensional histograms are calculated; (i) the photon count number distribution collected in counting time intervals of 100 $\mu$s (FIDA) and (ii) the delay time distribution (FLA). Furthermore, the two-dimensional FILDA histogram is built up according to the present invention, comprising both, the photon count numbers and the delay times integrated over the counting time interval of 100 $\mu$s.

From FCS measurements the mean diffusion time of the fluorescent dyes MR121, EVOblue30 and Bodipy630/650 was determined to 200 $\mu$s. With a diffusion constant of D3×10$^{-6}$ cm$^2$/s this yields a radial 1/e$^2$-radius of 0.5 m (Rigler et al., Eur. Biophys. J. 22, 169–175, 1993). The time-averaged laser beam power under the objective was 200 $\mu$W.

Experimental Procedures

In order to gage the equipment, four different calibration measurements were performed; (i) daylight as a random source of photons to correct data for uneven channel width of tie TDC, (ii) scattered light of the incident laser from pure buffer or water samples to determine the IRP of the equipment, (iii) pure dye solution to determine the spatial brightness parameters of Eq. 9, and (iv) a measurement on pure water to obtain independent estimates of the dark and scattered Raman count rates. The latter are regarded as two "species" which are always present. They both have Poissonian count number distributions but extremely different delay time distributions.

Figure 1B:
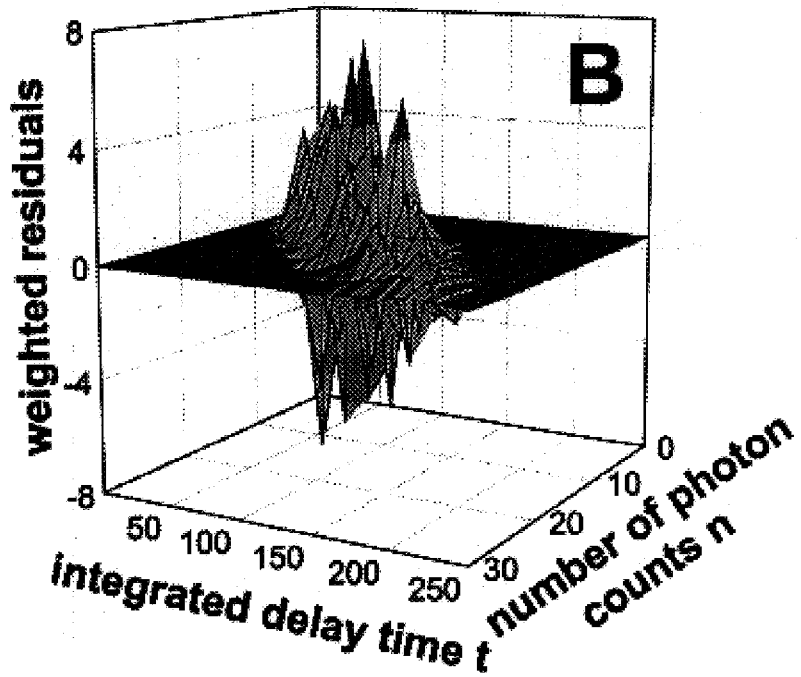

As an example FIG. 1A shows the obtained FILDA histogram of an approximately 1 nM Bodipy630/650 solution. The x-axis represents the sum of delay times while the y-axis represents the photon count number as described above. Data for this histogram were collected for 2 s. Fitting this two-dimensional histogram to the Fourier transform of Eq. 11 yields the concentration or mean number of molecules in the detection volume, c=2.3, the specific brightness, q=23.2 kHz, and the fluorescence lifetime, $\tau$=3.3 ns, which is in agreement with the values determined by FIDA and FLA alone (data not shown) as well with previously reported lifetimes for Bodipy630/650. To judge the goodness of the fit, FIG. 1B shows the weighted residuals, $\sqrt{W(n,t)}[\hat{P}(n,t)-P(n,t)]$, with at least square value of $\chi^2$=1.1.

Data Simulations

Real samples comprising a mixture of molecules, which express deliberately chosen parameters (brightness and fluorescence lifetime values), are difficult to prepare. Therefore, certain evaluations were performed using simulated data. A number of sets of histograms for FILDA (present invention), FIDA (prior art), and FLA (prior art) have been simulated according to the algorithm described in detail elsewhere (Palo et al. Biophys. J. 79, 2858–2866, 2000; the contents of which are herein incorporated by reference). This algorithm includes random walk of individual molecules and a conversion of brightness integrals into random count numbers. As a modification of this algorithm, a random detection delay time depending on the lifetime of the given species is additionally assigned to each photon, and the IRF used in simulations has been selected identical to that of the real experiment. The random count numbers and detection delay times obtained were subsequently used to calculate histograms for FILDA, FIDA, and FLA.

The simulations are considered to be an adequate tool for estimating statistical errors of the extracted parameters. For this purpose, typically N=40–100 realizations of experiments with a given set of molecular parameters were simulated.

Fitting

Experimental or simulated FILDA (present invention), FIDA (prior art), and FLA (prior art) distributions are fitted using a standard Marquardt algorithm. The fitting program designed for FIDA basically uses Eq. 8, while that for FILDA rests upon Eq. 11. The fit curve for FLA is, as mentioned above, significantly simpler than in FILDA because it relies only on calculating P(t|1).

Biochemical System: The Calmodulin-Peptide Interaction

Calmodulin (MW 16.7 kDa) is a regulatory protein involved in a variety of Ca$^{2+}$-dependent cellular signaling pathways (Klee, Biochemistry 27, 6645–6653, 1988). Structures at atomic resolution have identified two similar domains with two Ca$^{2+}$-binding sites each (Babu et al., Nature 315, 37–40, 1985; Babu et al., J. Mol. Biol. 204, 191–204, 1988; Chattopadhyaya et al., J. Mol. Biol. 228, 1177–1192, 1992, Wilmann et al., Cell Mol. Biol. Noisyle-grand, 46, 883–894, 2000), which for calmodulin in solution are connected by a flexible linker (Ikura et al., Cell Calcium 13, 391–400, 1992). Upon binding of $Ca^{2+}$ those residues that create the binding site for most target proteins get exposed to the solvent. The relevant peptide sequence from one of the target proteins (e.g. smooth muscle myosin light chain kinase, sm-MLCK) is KRRWKKNFIA and was chosen as the target peptide. At the C-terminus an additional Lysine was introduced in order to label the C-terminus with a dye (e.g. MR121). Since the predominant interaction sites of the target peptide (which interacts with both calmodulin domains) have been identified as the C- and the N-terminus (Meador et al., Science 257, 1251–1255, 1992; Meador et al., Science 262, 1718–1721, 1992), the molecular environment of the dye should change upon binding. Fluorescence lifetime, molecular intensity as well as FILDA data should therefore indicate a binding event.

Calmodulin was purchased from BIOMOL (from bovine brain, LOT# P4639c, 1 mg, lyophilized). The protein was dissolved in 25 mM Tris/HCl pH 8 and stored in aliquots at 4° C. The peptide (H-KRRWKKNFIAK-$NH_2$) was synthesized at EVOTEC and labeled with oxazine dye MR121 (Abs. max.=661 nm) at the C-terminal Lysine The buffer used throughout all experiments included 25 mM Tris/HCl pH 8, 1 mM $CaCl_2$, 100 mM KCl, and 0.05% Pluronic. Calmodulin and the fluorescently labeled peptide were incubated for 10 minutes prior to the measurement.

Fluorescent Dyes and Probe Handling

The dyes used were Bodipy630/650 (Molecular Probes, Eugene, Oreg., USA), Cyanine 5 (Cy5) (Amersham Pharmacia Biotech, Uppsala, Sweden), MR 121 (Roche Diagnostics, Penzberg, Germamy), and EVOblue 30 (EVOTEC BioSystems AG, Hamburg, Germany), which all have their excitation maximum around 635 nm. Dye solutions were prepared in ultrapure water.

As samples the fluorescent probes were prepared at concentrations around 1 nM. Because of possible adsorption of the molecules to glass surfaces, it is not adequate to determine their concentration values from dilution ratios; a much better estimate is given by FILDA itself since this method yields absolute concentrations. All experiments were carried out at 22° C. room temperature.

Results

A new method is best evaluated when it is compared to known methods on the basis of statistical errors obtained from simulated data or from simple test experiments which utilize the same equipment and the same sequence of photon counts. Therefore, the method according to the present invention (FILDA) was applied in a first step to different dye solutions and mixtures and the results were compared with those from FLA and FIDA.

Test Experiments and Data Simulation

At first, a series of 40 measurements on a 2:1 dye mixture of EVOblue™30 and MR121 with a total dye concentration of approximately 1 nM was performed collecting data in parallel for FILDA, FIDA, and FLA. This series of experiments, with duration of $T_c$=2 s each, was repeated in simulations using similar molecular parameters. All data were fitted with a varying number of fixed parameters which were predetermined from experiments on the respective single dye solutions. The estimated parameters for all three methods are compiled in Table 1. In the particular case of single species, FILDA is in no way statistically more accurate than a simple combination of FIDA and FLA. This can be expected since all molecules are identical and one has nothing to gain from grouping delay times according to bursts from individual molecules. However, regarding the mixture of two dyes the fits over all data sets resulted in different mean values and statistical errors of the numbers of molecules per confocal volume, $c_1$ and $c_2$, their brightness values, $q_1$ and $q_2$, and lifetimes, $\tau_1$ and $\tau_2$, depending on the method and the number of free parameters. In Table 1 these errors are denoted in parenthesis in terms of the ratio of standard deviation to mean value (coefficient of variation, CV). It once again has to be mentioned, that prior art FLA only reveals the products, $c_1 q_1$ and $c_2 q_2$, instead of $c_1$ and $c_2$. If $c_1$ and $c_2$ are the only two parameters which are subject to fitting, i.e. both brightness and/or lifetime values are fixed to the predetermined values from Table 1, FILDA and FLA are nearly equal in accuracy while FIDA has higher CV values. This strategy can be applied in a number of biological assays monitoring for instance the binding of two molecules one of which is fluorescent, where one can indeed determine specific quantities of the free and bound state of the fluorescent compound in advance and fit only the two concentrations. However, very often this scheme cannot be used but a higher number of parameters has to be fitted. This may be due to the fact that there are multiple binding sites involved and the specific brightness of the complex depends on the extend of binding and may hence not be fixed. Another example occurs in drug screening where the effect of certain chemical or natural compounds is tested against a biological target. The compounds are mostly assumed to be non-fluorescent but in some cases turn out to be autofluorescent. These samples can be fitted to a 2+1 component model with additional parameters characterizing the autofluorescent compound but which are not known beforehand.

Here, the superiority of the present invention FILDA becomes apparent. If there are four free parameters, e.g. when the two lifetime parameters are as well subject to fitting, the statistical errors of FILDA compared to FLA are reduced by a factor of about two. This factor is even higher when the statistical errors are compared with those from FIDA and free running brightness values. Moreover, in the case of six fitted parameters, FILDA still gives convincing results with low CV values.

TABLE 1

Coefficients of Variance (CV's) of FILDA (invention), FLA (prior art), and FIDA (prior art) on a dye mixture of MR121 and Evoblue 30 at the data collection time of 2 s: comparison of experimental and simulated data

| | 2 free | | 4 free | | | | 6 free |
|---|---|---|---|---|---|---|---|
| | FILDA | FLA[a] | FIDA | FILDA | FLA[a] | FILDA | FIDA | FILDA |
| $\frac{\sigma_{c_1}}{\sigma_1}$, % | 7.0 (5.9) | 5.1 (3.0) | 14.7 (14.2) | 11.8 (10.4) | 20.1 (16.7) | 7.5 (6.5) | x (35.2) | 15.1 (12.4) |

TABLE 1-continued

Coefficients of Variance (CV's) of FILDA (invention), FLA (prior art), and FIDA (prior art) on a dye mixture of MR121 and Evoblue 30 at the data collection time of 2 s: comparison of experimental and simulated data

| | 2 free | | | 4 free | | | 6 free | |
|---|---|---|---|---|---|---|---|---|
| | FILDA | FLA[a] | FIDA | FILDA | FLA[a] | FIDA | FIDA | FILDA |
| $\frac{\sigma_{c_2}}{c_2}$, % | 5.2 (4.0) | 5.8 (3.4) | 9.9 (6.7) | 9.0 (5.8) | 17.2 (15.0) | 9.3 (7.4) | x (23.9) | 12.6 (8.9) |
| $\frac{\sigma_{q_1}}{q_1}$, % | # | — | # | # | — | 7.2 (4.0) | x (11.4) | 9.1 (5.1) |
| $\frac{\sigma_{q_2}}{q_2}$, % | # | — | # | # | — | 8.0 (7.5) | x (30.8) | 7.4 (8.5) |
| $\frac{\sigma_{\tau_1}}{\tau_1}$, % | # | # | — | 4.9 (4.6) | 11.7 (12.6) | # | # | 5.1 (4.7) |
| $\frac{\sigma_{\tau_2}}{\tau_2}$, % | # | # | — | 6.8 (4.7) | 14.3 (16.0) | # | # | 8.4 (8.3) |
| $\chi^2$ | 1.3 1.0 | 3.8 1.3 | 0.8 0.8 | 1.3 1.0 | 3.5 1.1 | 1.3 1.1 | x 06 | 1.3 1.1 |

Figure 2:
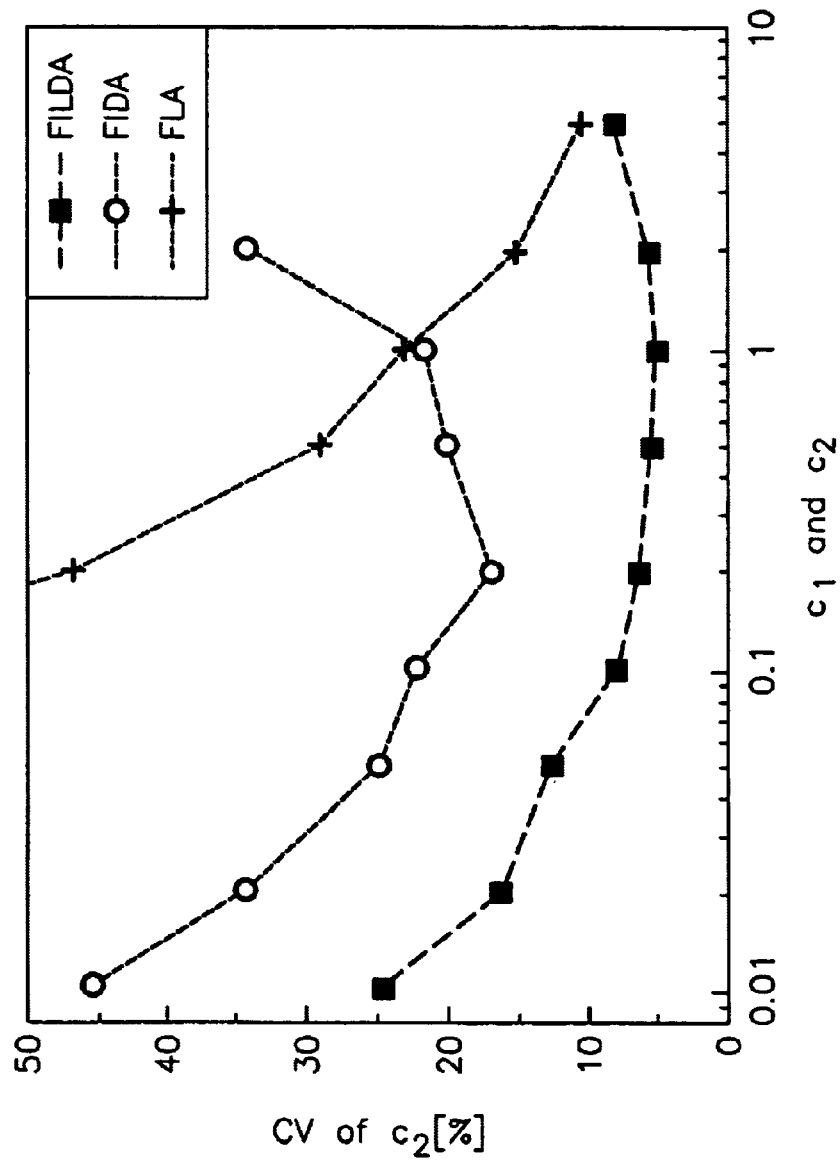
FIG. 2: Dependency of the CV's of FILDA (invention), FLA (prior art), and FIDA (prior art) an the fluorescent species concentration. 100 random histograms for each of the three methods were simulated for a 1:1 mixture of two fluorescent species at 20 s data collection time. The input parameters for the simulation were: concentration $c_1=c_2$ (x-axis), brightness $q_1$=30 kHz and $q_2$=15 kHz, lifetime $\tau_1$=3.0 ns and $\tau_2$=1.5 ns. All parameters ($c_1, c_2, q_1, q_2, \tau_1, \tau_2$ in FLDA; $c_1, c_2, q_1, q_2$ in FIDA and $c_1q_1, c_2q_2, \tau_1, \tau_2$ in FLA) were subject to fitting. The CV of the concentration value, $c_2$, of the second (weaker) component is plotted on this graph. Analysts of 100 histograms yields 7.1 percent accuracy of standard errors.

CV's were calculated over 40 repeated rneasurexneots. The mean results of analysis of experimental data were used as input to simulation algorithm: concentration $c_1$ = 0.24 and $c_2$ = 0.44, brightness $q_1$ = 17.5 kHz and $q_2$ = 7.5 kHz, lifetime $\tau_1$ = 1.72 ns and $\tau_2$ = 0.54 ns.
[a]: FLA yields $c_1 q_1$ and $c_2 q_2$, rather than $c_1$ and $c_2$;
x: analysis resulted in CV's above 50%;
( ): CV's of analysis on simulated data;
: fixed io the best known values However, from a practical point of view the question arises whether FILDA holds this high accuracy over a wide range of concentrations. Therefore, a series of 100 histograms was simulated for FILDA (present invention), FIDA (prior art), and FLA (prior art) for different concentrations of a 1:1 mixture of two fluorescent species and the results were compared again. A two-fold difference in the specific brightness ($q_1$=30 kHz and $q_2$=15 kHz) as well as in the lifetime ($\tau_1$=3.0 ns and $\tau_2$=1.5 ns) was selected but an equal diffusion tine (200 $\mu$s) for both species. All histograms were fitted to a two component model with all parameters being subject to fitting. Since at very low as well as at very high concentrations all methods had difficulties to resolve the species unambiguously with a data acquisition time of $T_c$=2 s, this time was prolonged to $T_c$=20 s. FIG. 2 shows the dependency of the statistical error of all three methods on the fluorescent dye concentration, represented by the CV values of the weakest signal, $c_2$. Within a concentration range of c<5 molecules per measurement volume, FILDA reveals the lowest error while FLA only at significantly higher concentrations is statistically more accurate. This is not surprising because FLA solely depends on the number of detected photons which linearly scales with the concentration. Contrary, FILDA and FIDA sense the relative fluctuations of the fluorescence signal which are reduced according to $\propto c^{-1/2}$. At extremely low concentrations the fluorescence signal basically consists of rare single-molecule events which may eventually not be detected during a data collection time of 20 s. However, with a longer acquisition time these rare events are much better approachable with a fluctuation method like FILDA than with conventional FLA.

Figure 3:
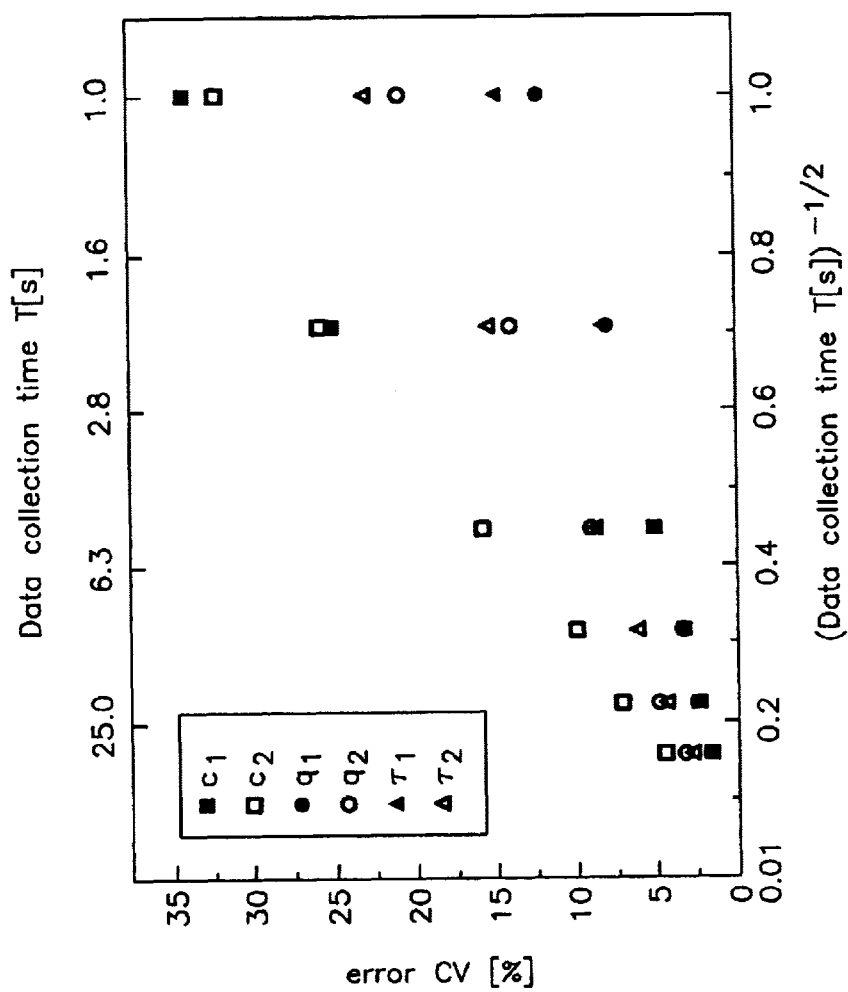
FIG. 3: Dependency of the CV's of FILDA on the data collection time, T (upper x-axis). The analysis was performed on 100 simulated histograms of a 1:1 dye mixture with the following input parameters: concentration $c_1=c_2$= 0.2, brightness $q_1$=30 kHz and $q_2$=15 kHz, lifetime $\tau_1$=3.0 ns and $\tau_2$=1.5 ns. Analysis of 100 histograms yields 7.1 percent accuracy of standard errors. The lower x-axis shows $T^{-1/2}$ to clarify the linear dependency.

The linear dependency of the statistical errors of different FILDA parameters on $T_c^{-1/2}$ is shown in FIG. 3. The CV values plotted result from the same simulation scheme as above but with a single concentration of $c_1$=$C_2$=0.2. It clearly can be seen that reasonable CV values may already be achieved with data acquisition times of 10 s, even though no parameter has been fixed, i.e. no a priori information has been used.

Biochemical System

The experimental utilization of FILDA will be demonstrated by the determination of the binding constant of the above introduced Calmodulin-peptide interaction. For this purpose, a titration experiment was carried out, keeping the labeled peptide (H-KRRWKKNFIAK-NH$_2$(MR121)) concentration constant at 2.5 nM, while Calmodulin was subject to titration (0, 0.01 nM 0.1 nM, 1 nM, 3 nM, 10 nM, 30 nM, 0.1 $\mu$M, 0.3 $\mu$M, 1 $\mu$M, 10 $\mu$M, 50 $\mu$M). All experiments were performed under identical conditions, i.e., the same buffer, the same excitation power, and the same data acquisition time of 2 s per measurement, repeated 10 times per sample.

As the first step, the lifetime $\tau_{free}$=1.90±0.02 ns and the specific brightness $g_{free}$=6.5±0.3 kHz were determined from a single component analysis applied to the pure peptide solution. Addition of excess Calmodulin (50 $\mu$M) to 2.5 nM peptide resulted in a sample with the majority of the peptide bound to Calmodulin. The complex was characterized both by a longer fluorescence lifetime $\tau_{bound}$=3.00±0.01 ns and a higher specific brightness $q_{bound}$=15.0±0.6 kHz compared to the free peptide indicating changes of the molecular environment of the dye (e.g. decrease of the polarity). This mixture was then analyzed by all three methods (FILDA, FIDA, and FLA) using a two-component fit with $\tau_{free}$ and/or $q_{free}$ fixed, depending on the method.

As the next step, a two component analysis was applied to the whole series of Calmodulin concentrations. In these studies, the lifetime and brightness parameters were fixed to the above values for the bound and unbound peptide. In this way, FILDA determines the concentrations, $c_{bound}$, of the bound peptide, i.e., the Calmodulin-peptide complex, and, $c_{unbound}$, of the unbound, i.e., free peptide. This allows the calculation of the fraction, $f_{bound}(c_{bound}/(c_{bound}+c_{bound}))$, of bound peptide, which is plotted against the concentration of added Calmodulin in FIG. 4 (black spots, error bars result from averaging over 10 measurements). The solid line shows a hyperbolic fit to the data, yielding a binding constant for the Calmodulin-peptide interaction of $K_D=38\pm3$ nM. Comparable binding curves were obtained by FLA and FIDA (data not shown) with similar $K_D$ values of $17\pm1$ nM and $29\pm4$ nM, respectively. These values agree well with affinities reported in literature (Barth et al., J. Biol. Chem. 273, 2174–2183, 1998) and demonstrate that FILDA is a suitable method for monitoring the reactivity of a biochemical system.

To obtain some information about the statistical accuracy of this experiment with respect to possible drug screening applications, the Z'-value of the binding curve can be calculated. This is accomplished via the mean values, $f_{high}$ and $f_{low}$, and their standard deviations, stdev($f_{high}$) and stdev($f_{low}$), of the fraction, $f_{bound}$, of bound peptide resulting from the two component analysis of the bound peptide solution (50 μM Calmodulin, high) and of the pure peptide solution (0 Calmodulin, low), respectively.

$$Z' = 1 - \frac{3*[stdev(f_{high}) + stdev(f_{low})]}{f_{high} - f_{low}} \quad (13)$$

The Z'-value relates the statistical errors of determining $f_{bound}$ to its dynamic range. It is therefore a very important statistical parameter to judge the feasibility and efficiency of a certain readout and analysis method to validate the binding degree or in general any reaction degree of a biochemical system. Its maximum value is Z'=1.0, while in general a prerequisite of Z'>0.5 is needed in drug screening applications.

Figure 4:
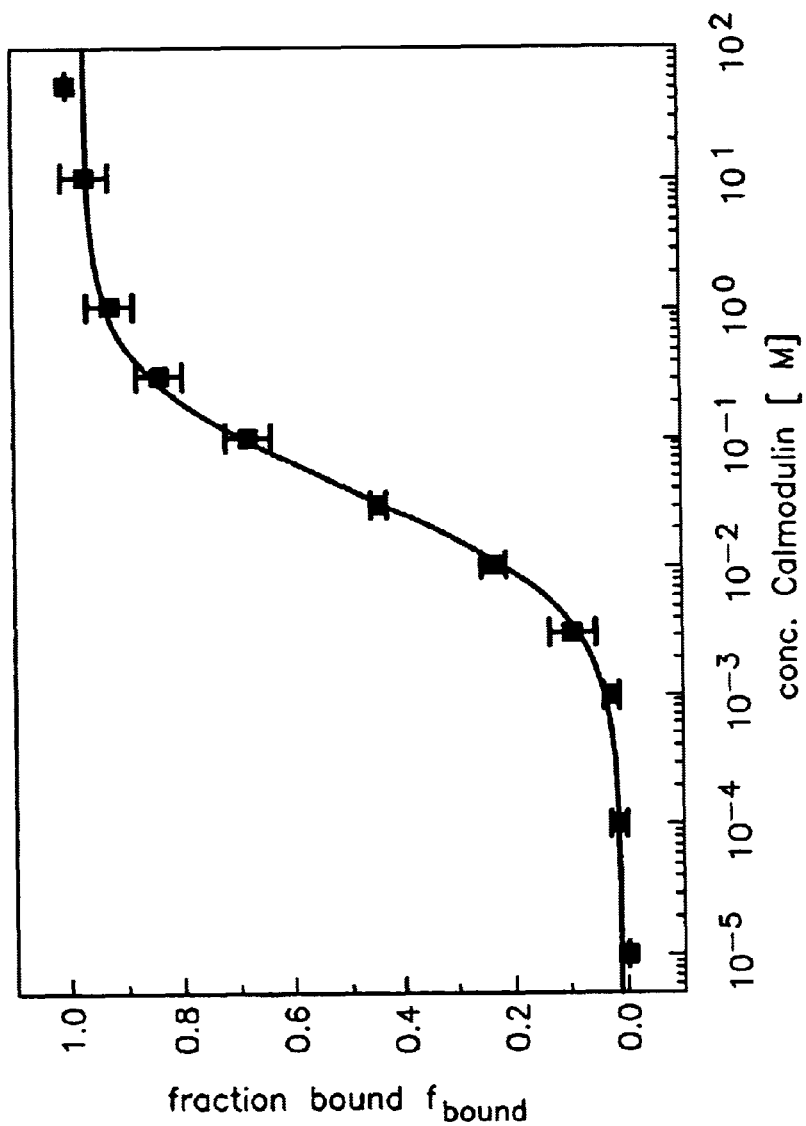
FIG. 4: Binding of the labeled target peptide. H-KRRWKKNFIAK-NH$_2$, to calmodulin as monitored by FILDA (data collection time, T=2 s, error bars from averaging over 10 repeated measurements). The solid curve results from a hyperbolic fit to the data, yielding a binding constant of $K_D$=38±3 nM.

From FIG. 4 a Z'-value of $0.97\pm0.01$ is obtained for the Calmodulin-peptide interaction using the method according to the present invention and a data acquisition time of 2 s. For comparison, the application of prior art FLA and prior art FIDA reveals Z'-values of $0.92\pm0.02$ and $0.73\pm0.07$, respectively. With Z'-values close to one all methods are very well feasible to be used in drug screening.

However, drug screening applications are trying to minimize the readout time as far as possible. Thus, the Z'-values of FILDA of the Calmodulin-peptide interaction were determined for decreasing data acquisition times, T:Z'(T=1 s)=$0.85\pm0.04$, Z'(T=0.5 s)=$0.81\pm0.05$, Z'(T=100 ms)=$0.54\pm0.11$, and Z'(T=50 ms)=$0.35\pm0.16$ (at data acquisition times below 10 ms FILDA becomes not applicable due to negative Z'-values). Therefore, the present invention "FILDA" is a method that fulfills the prerequisites for efficient drug screening even at read out times below 1 s down to 100 or 50 ms.

EXPERIMENT 2

As the basic part of the equipment, an epi-illuminated confocal microscope is used, combined with a pulse laser, a time to amplitude converter (TAC) and a data acquisition card. For each photon detected, two time intervals are synchronously determined and saved: the time passed from the previous photon count and the time interval between the photon detection and the consequent laser pulse. The first time interval is measured in units of the card clock period of 50 ns while the time resolution of the TAC is 70 ps. From raw data, at given width of the counting time interval (usually, 100 μs) and given resolution value of the delay time (either 280 or 560 ps), one- and two-dimensional distributions for FIDA (prior art), FLA (prior art) and FILDA (present invention) were calculated. In a series of measurements, at least one measurement was performed with the detector monitoring the daylight as a random source of photons, in order to correct other data for uneven channel width of the TAC. Another measurement with the detector monitoring the scattered light of the incident laser from milky samples was performed to determine the point spread function of the equipment. Also, a measurement on pure water was useful to obtain independent estimates of the dark and scattered Raman count rates which are considered as two "species" always present. They both have Poissonian count number distributions but extremely different delay time distributions As samples, a series of aqueous pure dye solutions were prepared at concentrations around $10^{-9}$ M, as well as their mixtures at a concentration ratio approximately 1:1. Because of possible adsorption of the dyes to glass surfaces, it is not adequate to determine concentration values of the dyes from dilution ratios; a much better estimate is FILDA itself. The dyes used were bodipy 630, Cy5, and UR 121. Experiments were carried out at room temperature.

Figure 5A:
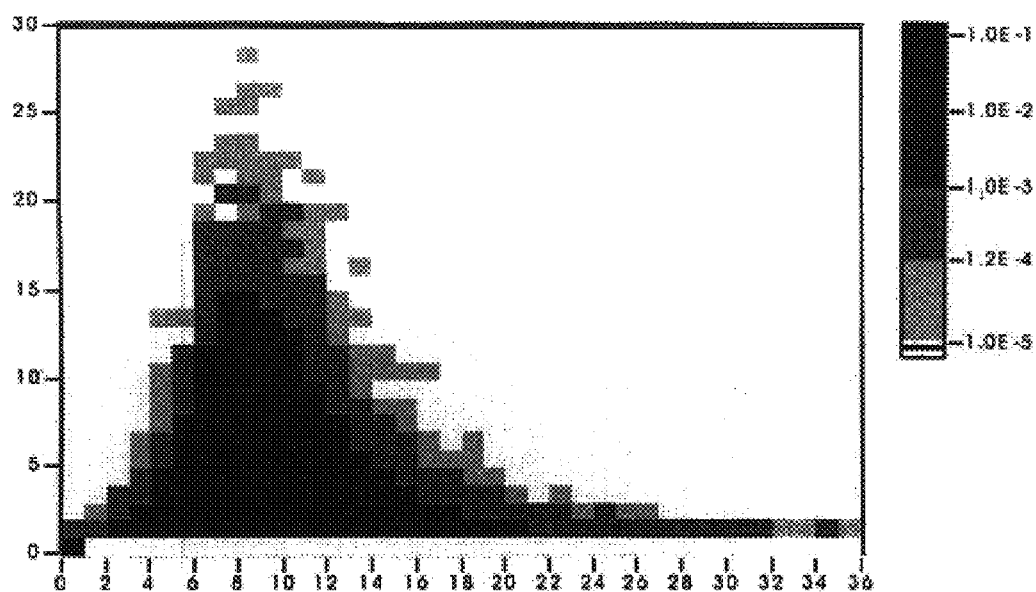
FIG. 5: Illustration of intensity graphs of histograms of experiment 2. X-axes is the averaged pulse to photon delay time; y-axes is the number of photon counts. A darker intensity corresponds to a higher number of events.
Figure 5B:
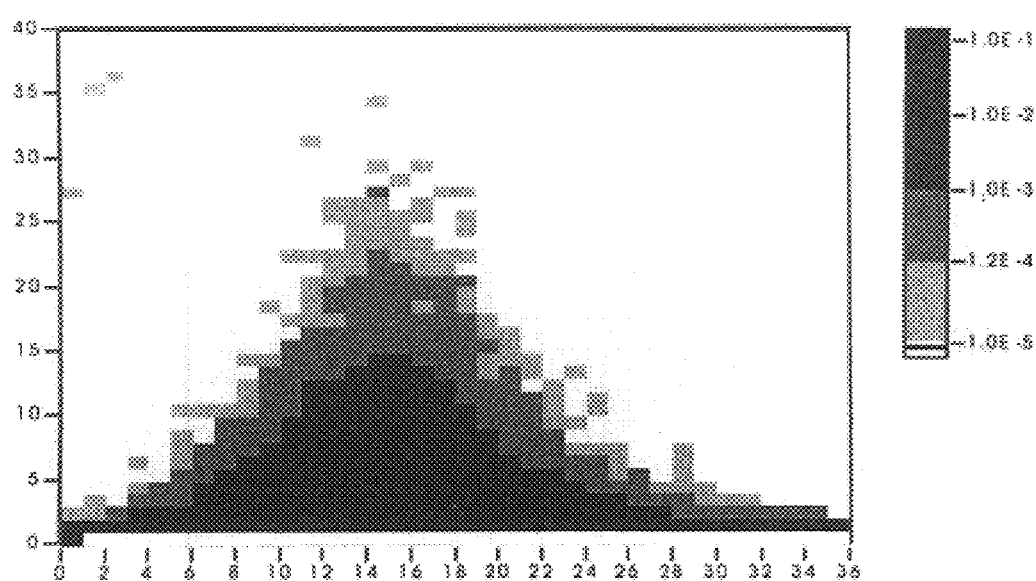
Figure 5C:
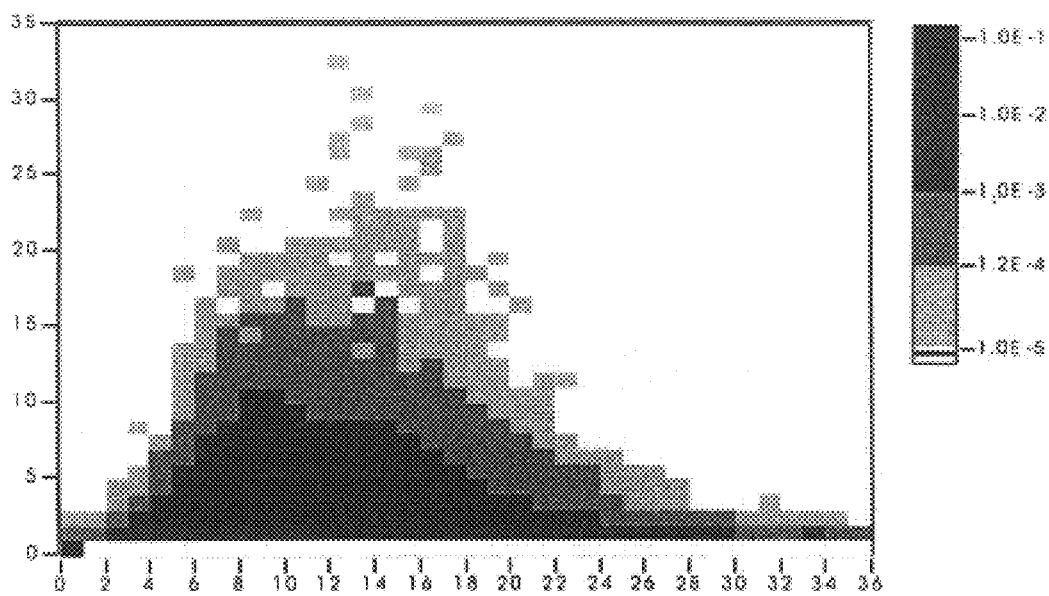
Figure 6:
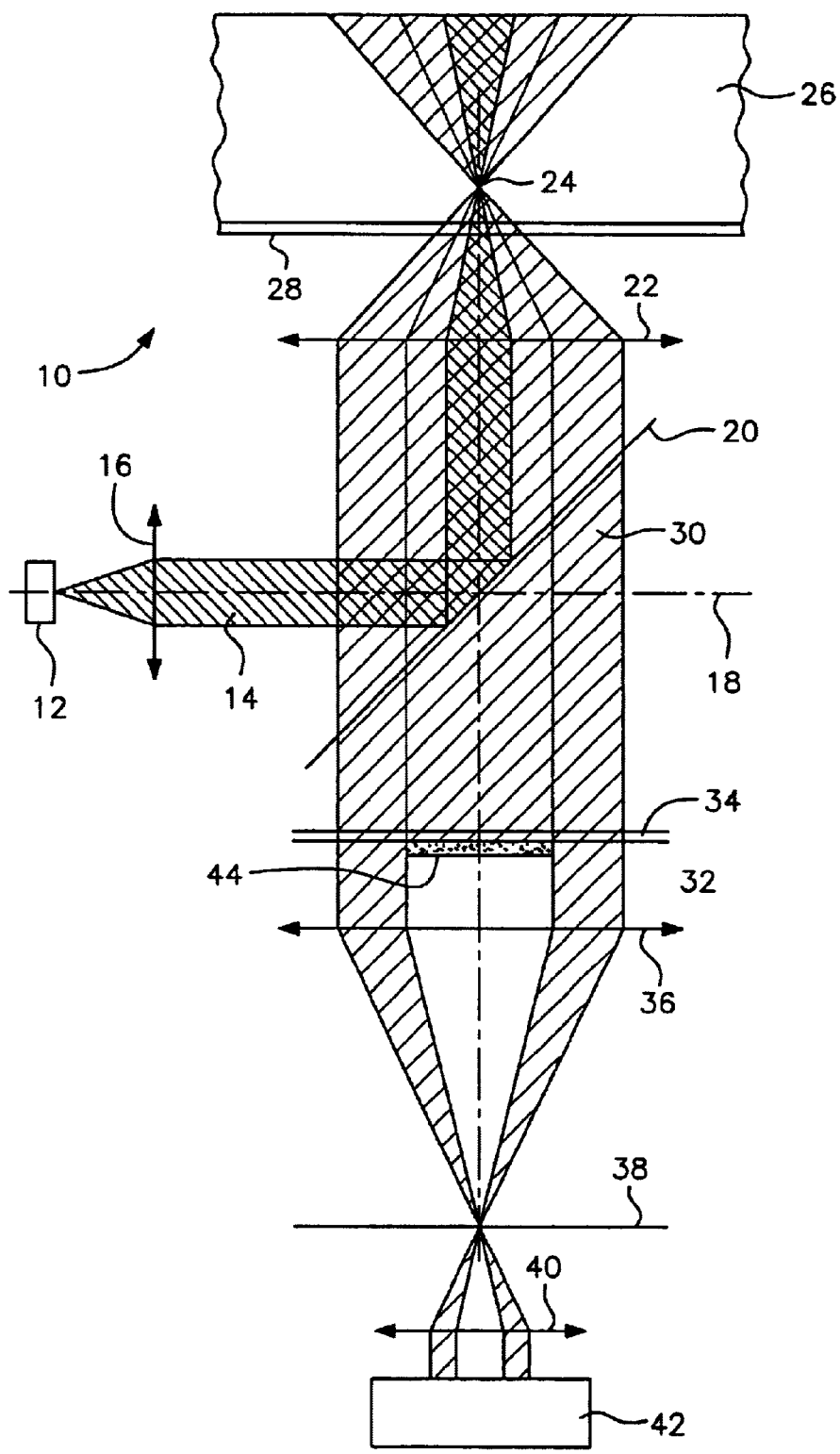
FIG. 6: shows one embodiment of an apparatus adapted for use in performing the method according to the present invention. Apparatus 10 comprises a laser 12 which serves as a light source for illuminating the sample by a bundle of coherent monochromatic excitation radiation 14. Excitation radiation 14 is paralleled by a lens 16 and reaches a dichroic mirror 20. Preferably, the angle between the optical axes 18 and the dichroic mirror 20 is 45°. The dichroic mirror 20 reflects the excitation radiation 14 in direction of an objective lens 22 having its focus 24 within a sample volume 26. Sample volume 26 and objective lens 22 are preferably separated from each other by a transparent cover glass 28, e.g. by the bottom of a commercially available micro-liter plate which houses the sample. The sample preferably includes fluorescently labeled molecules or other particles. Due to excitation by an appropriate excitation radiation 14, the molecules or other particles present in the sample emit radiation 30. Emission radiation 30 passes the objective lens 22 and reaches the dichroic mirror 20 which is transparent for emission radiation 30. Thereafter, emission radiation passes a filter 34 and a collimator lens 36 on the optical axes 32. A pinhole 38 is situated in the focus of collimator lens 36. Emission radiation 30 passing the pinhole 38 reaches a further lens 40 and, thereafter, is detected by the photo-detector 42. Within the pathway of emission radiation 30, in particular between dichroic mirror 20 and photo-detector 42, an opaque means 44 is provided through which a central part of the emission radiation 30 cannot pass. This central part of the emission radiation 30 stems from areas on the optical axes 32 in front of or behind the focus 24 of the excitation radiation 14. Only emission radiation 30 that stems from the focus 24 or its direct neighborhood passes the pinhole 38 and reaches photo-detector 42. Instead of placing an opaque means 44 within the pathway of emission radiation 30, the pathway of excitation radiation 14 is also suitable for positioning an opaque means 44. In particular, an opaque means 44 can be positioned between laser 12 and dichroic mirror 20. The use of an opaque means 44 in the method according to the present invention as described in detail herein improves the signal-to-noise ratio.

FIG. 5 illustrates intensity graphs of measured histograms of the present experiment. X-axes is the averaged pulse to photon delay time, y-axes is the number of photon counts, and a higher intensity corresponds to a higher number of events. In FIG. 5, three examples of the measured distributions $M\hat{P}(n,t)$ are presented as intensity graphs, two examples for single species and the third one for their mixture (M is the total number of counting time interval per experiment). The weighted residuals of fitting (not shown) are scattered randomly except that often the data points (n,t)=(1,0) and (1,1) (corresponding to the lowest part of the raising edge of the excitation pulse) deviate from the fit curve by up to 5 units of standard deviation. The upper graph visualizes the distribution #12 measured on a Cy5 solution (having the shortest lifetime among the three dyes), the middle graph is the distribution #7 measured on a Bodipy 630 solution (having the longest lifetime), and the lowest graph is the distribution #30 corresponding to a mixture of these dyes. In fact, the x-argument of the function which is technically fitted is the sum rather than the average delay time, but the distribution function of the average delay time seems visually more informative.

Full width at half maximum (FWHM) of the response function of this experiment is nearly 2 ns which is significantly wide compared even to the pulse period of 10 ns and exceeds lifetimes of two dyes out of the three, but it is still applicable to resolve two components with twofold lifetime difference. Dark and scattering count rates from water were determined to be 0.20 and 0.29 kHz respectively which were fixed at these values when fitting data from fluorescent samples.

It is possible to estimate values of spatial adjustment parameters $a_1$ and $a_2$ by the present invention from data on single species, but because of the relatively low absolute values of q obtainable with the low power pulse laser, the corresponding statistical errors are high, approximately 20 percent. However, the results of subsequent analysis only weakly depend on exact values of the adjustment param eters. Therefore, $a_1$ and $a_2$ at rounded values determined by FIDA at continuous laser excitation, $a_1 = -0.40$ and $a_2 = 0.08$.have been simply fixed.

After fixing values of dark and scattering count rates and spatial parameters, the only parameters of fitting are concentration (c), specific brightness (q) and lifetime ($\tau$) per each species. Indeed, the distributions obtained from single species could well be fitted assuming single species while the distributions obtained from two-component mixtures required a two-component analysis in order to result in randomly scattered residuals. It has been shown already after the first test experiments that the new fluorescence fluctuation method presented can be used as a sensitive method for separating two fluorescent components, determining their concentrations and characterizing them in terms of specific brightness and lifetime of fluorescence. Note that statistical errors can be significantly lowered by fixing some more parameters at values determined beforehand, this is a standard grip in drug screening.

EXPERIMENT 3

Using the weights by Eq. 12, theoretical errors of the present invention have been calculated in a number of selected cases and compared with the corresponding errors of fluorescence intensity distribution analysis (FIDA) and fluorescence lifetime analysis (FLA). Some of the results of the two-component cases are presented in Table 2. It is worth pointing out that the method according to the present invention is not only a qualitatively stronger method than FIDA or FLA (for species are recognized by the two specific quantities, q and $\tau$) but within its optimal concentration range, its statistical errors are lower. Only at significantly high concentration values where FILDA and FIDA, as essentially fluctuation methods, lose their power while FLA does not, FLA is statistically the most accurate out of the three methods.

TABLE 2

Theoretical errors of two-component FILDA (present invention), FIDA (prior art) and FLA (prior art)
In all cases, T = 100 $\mu$s, $c_1 = c_2$, $q_2 = 50$ kHz, $q_2 = 25$ kHz, $\tau_1 = 3$ ns, $\tau_2 = 1.5$ ns, dark count rate 0.2 kHz, scattered count rate 1 kHz, duration 20 s.

| | Percent error of FILDA of . . . | | | | | | Percent error of FIDA of . . . | | | | Percent error of FLA of . . . | | | |
|---|---|---|---|---|---|---|---|---|---|---|---|---|---|---|
| $c_1\ c_2$ | $c_1$ | $c_2$ | $Q_1$ | $q_2$ | $\tau_1$ | $\tau_2$ | $c_1$ | $c_2$ | $Q_1$ | $q_2$ | $c_1q_1$ | $c_2q_2$ | $T_1$ | $\tau_2$ |
| 0.05 | 6.1 | 6.5 | 3.8 | 3.9 | 1.7 | 3.1 | 17 | 20 | 4.3 | 11 | 17 | 34 | 6.3 | 13 |
| 0.2 | 2.9 | 3.2 | 1.6 | 2.0 | 0.80 | 1.6 | 11 | 11 | 2.9 | 7.2 | 7.6 | 15 | 2.8 | 5.6 |
| 1.0 | 2.0 | 2.2 | 0.88 | 1.5 | 0.50 | 1.2 | 14 | 13 | 3.3 | 9.1 | 3.3 | 6.5 | 1.2 | 2.4 |
| 5.0 | 3.3 | 3.4 | 1.0 | 2.1 | 0.69 | 2.4 | 52 | 44 | 11 | 38 | 1.4 | 2.9 | 0.53 | 1.1 |

TABLE 3

Results of FILDA experiments according to the present invention
Error values presented are statistical errors corresponding to theoretical weights

| Sample | Data collection time, s | # of experiment in a series | Concentration c | Specific brightness q, kHz | Lifetime t, ns |
|---|---|---|---|---|---|
| Cy5 | 3.5 | 12 | 1.71 ± 0.02 | 20.2 ± 0.3 | 0.724 ± 0.004 |
| | | 13 | 1.84 | 19.7 | 0.721 |
| | | 14 | 1.74 | 20.0 | 0.719 |
| UR125 | 13.1 | 21 | 0.498 ± 0.005 | 17.5 ± 0.2 | 1.830 ± 0.008 |
| | | 22 | 0.460 | 17.7 | 1.836 |
| | | 23 | 0.463 | 18.3 | 1.805 |
| Mixture of Cy5 and UR125 | 5.1 | 36 | 0.66 ± 0.05 | 19.9 ± 0.5 | 0.724 ± 0.028 |
| | | | 0.62 ± 0.05 | 16.1 ± 0.5 | 1.72 ± 0.06 |
| | | 37 | 0.71 | 20.1 | 0.716 |
| | | | 0.54 | 16.3 | 1.72 |
| | | 38 | 0.64 | 21.6 | 0.685 |
| | | | 0.60 | 14.9 | 1.61 |

What is claimed is:

1. A method for characterizing samples having fluorescent particles, comprising the steps of:
    exciting particles in a measurement volume to emit fluorescence by a series of excitation pulses,
    monitoring the emitted fluorescence by detecting sequences of photon counts using a detection means,
    determining numbers of photon counts in counting time intervals of given width,
    determining in said counting time intervals detection delay times of the photon counts relative to the corresponding excitation pulses,
    determining a function of said detection delay times,
    determining a probability function of at least two arguments, $\hat{P}(n, t, \ldots)$ wherein at least one argument is the number of photon counts and another argument is said function of detection delay times, and
    determining from said probability function $\hat{P}(n, t, \ldots)$ a distribution of particles as a function of at least two arguments, wherein one argument is a specific brightness of the particles, or a measure thereof, and another argument is a fluorescence lifetime of the particles, or a measure thereof.

2. The method according to claim 1 wherein said function of said detection times is invariant in respect of the order of detection delay times of photon counts detected in the same counting time interval.

3. The method according to claim 1 wherein said function of said detection delay times is a sum or a mean.

4. The method according to claim 1 wherein said detection delay times of photon counts relative to the corresponding excitation pulses are expressed by integer numbers having a known relationship to the detection delay times, in particular a quasi-linear relationship.

5. The method according to claim 4 wherein said function of detection delay times is a sum or a mean of said integer numbers.

6. The method according to claim 1 wherein said distribution function of particles is determined by fitting the experimentally determined probability function $\hat{P}(n, t, \ldots)$ by a corresponding theoretical probability function $P(n, t, \ldots)$.

7. The method according to claim 6 wherein the theoretical distribution $P(n, t, \ldots)$ is calculated through its generating function $$G_{P(n,t,\ldots)}(\xi, \eta, \ldots) = \sum_{n,t,\ldots}^{\infty} \xi^n \eta^t \ldots P(n, t, \ldots).$$

8. The method according to claim 6 wherein said distribution function of particles is determined by fitting the experimentally determined probability function $\hat{P}(n,t)$ by a corresponding theoretical probably function $P(n,t)$.

9. The method according to claim 6 wherein in calculations of the theoretical probability function $P(n, t, \ldots)$ the optical spatial brightness function $B(r)$ is accounted for by a separately determined relationship between spatial brightness $B$ and volume elements $dV$.

10. The method according to claim 9 wherein the relationship between the spatial brightness $B$ and volume elements $dV$ is expressed through a variable $u=\ln(B_0/B)$ by a relationship $$\frac{dV}{du} = A_0(1 + a_1 u + a_2 u^2)u^{a_3},$$

where $B_0$ is maximum brightness and $A_0$, $a_1$, $a_2$ and $a_3$ are empirical parameters of the spatial brightness function.

11. The method according to claim 1 wherein a temporal response function of the experimental equipment is considered in calculation of the theoretical distribution $P(n, t, \ldots)$.

12. The method according to claim 1 wherein a set of different probability functions $P(n, t, \ldots)$ is determined, each probability function relying on numbers of photon counts determined in counting time intervals of different widths.

13. The method according to claim 1 wherein said counting time intervals are consecutive in time.

14. The method according to claim 1 wherein said counting time intervals overlap.

15. The method according to claim 1 wherein a diffusion coefficient, or any other measure of diffusion, is another argument of said distribution function of particles.

16. The method according to claim 1 wherein concentrations of particles are selected to be approximately one or less particles per measurement volume.

17. The method according to claim 6 wherein a single, two or more photon detectors are used as said detection means.

18. The method according to claim 1 wherein at least two photon detectors are used as said detection means monitoring fluorescence of different wavelengths or polarization.

19. The method according to claim 1 wherein said fluorescent particles are characterized applying an homogeneous fluorescence assay.

20. The method according to claim 1 for use in diagnostics, high throughput drug screening, optimization of properties of molecules and identification of specific cell populations.

21. A confocal apparatus useful for performing the method according to claim 1, said confocal apparatus comprising:

a radiation source (12) for providing excitation radiation (14), an objective (22) for focusing the excitation radiation (14) into a measurement volume (26), a detector (42) for detecting emission radiation (30) that stems from the measurement volume (26), and an opaque means (44) positioned in the pathway (32) of the emission radiation (30) or excitation radiation (14) for erasing the central part of the emission radiation (30) or excitation radiation (14).

22. The method according to claim 8 wherein the corresponding theoretical probability function $P(n,t)$ is calculated through its generating function $$G_{P(n,t)}(\xi, \eta) = \sum_{n=0}^{\infty} \sum_{t=0}^{\infty} \xi^n \eta^t P(n, t).$$

23. The method according to claim 11 wherein said temporal response function is determined from a separate experiment.

24. The method according to claim 17 wherein the single, two or more photon detectors are either an avalanche photodiode or a photomultiplier.

* * * * *